United States Patent
Sun et al.

(10) Patent No.: US 10,428,405 B2
(45) Date of Patent: Oct. 1, 2019

(54) EXTRACTANT AND METHOD FOR EXTRACTING AND SEPARATING YTTRIUM

(71) Applicant: XIAMEN INSTITUTE OF RARE EARTH MATERIALS, Xiamen, Fujian (CN)

(72) Inventors: Xiaoqi Sun, Fujian (CN); Yanliang Wang, Fujian (CN); Yamin Dong, Fujian (CN)

(73) Assignee: XIAMEN INSTITUTE OF RARE EARTH MATERIALS, Xiamen, Fujian (CN)

( * ) Notice: Subject to any disclaimer, the term of this patent is extended or adjusted under 35 U.S.C. 154(b) by 464 days.

(21) Appl. No.: 15/081,344

(22) Filed: Mar. 25, 2016

(65) Prior Publication Data
US 2016/0348213 A1    Dec. 1, 2016

(30) Foreign Application Priority Data

May 25, 2015 (CN) .......................... 2015 1 0270369
Nov. 13, 2015 (CN) .......................... 2015 1 0777786

(51) Int. Cl.
*C22B 59/00* (2006.01)
*C07C 59/70* (2006.01)
(Continued)

(52) U.S. Cl.
CPC .............. *C22B 59/00* (2013.01); *C07C 59/70* (2013.01); *C07F 9/5407* (2013.01); *C22B 3/0005* (2013.01); *Y02P 10/234* (2015.11)

(58) Field of Classification Search
CPC ...................................................... C22B 59/00
See application file for complete search history.

(56) References Cited

FOREIGN PATENT DOCUMENTS

| CN | 1153836 C | * | 6/2004 |
| CN | 101050185 A | | 10/2007 |

(Continued)

OTHER PUBLICATIONS

Wang et al. Application of Bifunctional Ionic Liquid Extractants [A336][CA-12] and [A336][CA-100] to the Lanthanum Extraction and Separation from Rare Earths in the Chloride Medium, Want, Ind. Eng. Checm. Res. 2011, 50, 7534-7541 (Year: 2011)*

*Primary Examiner* — Melissa S Swain
(74) *Attorney, Agent, or Firm* — Novick, Kim & Lee, PLLC; Allen Xue (57) ABSTRACT

An extractant and a method for the extraction and separation of yttrium are disclosed in the invention. Cations of said extractant are selected from the group of quaternary phosphonium or quaternary ammonium, and the anion is sec-octylphenoxy acetate. The extractant has a simple composition, the formulated organic phase has stable properties and can be recycling used without significantly decreased concentration. The present invention used a mixed organic phase consisting of an extractant and a diluent to extract a rare earth feed liquid containing yttrium, and then washed and back extracted it with deionized water so that the consumption of acid and alkali in all the processes of extraction, washing and back extraction was avoided. Therefore, the extraction is carried out under a low acidity and a high extraction efficiency was ensured. The organic phase can be recycling used without saponification, so that no ammonia wastewater was produced in the processes.

14 Claims, 2 Drawing Sheets

(51) Int. Cl.
*C07F 9/54* (2006.01)
*C22B 3/26* (2006.01)

(56) References Cited

FOREIGN PATENT DOCUMENTS

| | | | |
|---|---|---|---|
| CN | 104087750 A | 10/2014 | |
| CN | 104195336 A | 12/2014 | |
| CN | 104862504 A | 8/2015 | |
| CN | 104946888 A | 9/2015 | |
| GB | 1300305 A | * 12/1972 | .......... C01F 17/0006 |

* cited by examiner

EXTRACTANT AND METHOD FOR EXTRACTING AND SEPARATING YTTRIUM

TECHNICAL FIELD

The present invention relates to the field of the extraction and the separation techniques of rare earth, and particularly relates to an extractant and a method for extracting and separating yttrium.

BACKGROUND ART

Yttrium as a heavy rare earth is widely used in rare earth-aluminum alloys, functional ceramics, lasers, phosphors, and other fields.

However, because yttrium has an ionic radius (0.88 Å) close to erbium (0.881 Å) of the lanthanide series, it possesses very similarly chemical properties to the lanthanides, specifically for heavier lanthanides, thus is difficult to be separated from the others.

According to existing processes, yttrium is mainly separated by an extraction and separation method using naphthenic acid (NA) as major extractant. The disadvantages of naphthenic acid method emerged for long-term industrial practices including: ① As a byproduct of the oil industry, naphthenic acid contains extremely unstable ingredients; ② naphthenic acid has a relatively high pKa value of 7.57. It is prone to react with high valence impurity metals such as iron (III), Th (IV), titanium (IV), zirconium (IV) to form solid naphthenates under high operational pH, thus leading to severe emulsification and loss of the extractants; ③ naphthenic acid reacts slowly with iso-octanol as a phase modifier, thereby leading saponification value to continually decrease and requiring regular supplement or even replacement of fresh extractants, which can produce a large amount of waste organic phases. Additionally, like those processes using other acidic extractants, the naphthenic acid process also requires saponification with alkalis (such as sodium hydroxide, aqueous ammonia, etc.) to form organic salts prior to extraction. In back-extraction process, it further consume a large amount of hydrochloric acid [Deqian Li, Chemical Engineering Problems in Hydrometallurgical Industry of Rare Earths, Progress in Chemistry, 7(3), 209-213, (1995)]. According to statistics, 6.5 to 8 moles of hydrochloric acid and 6 moles of alkali would be consumed per mole of yttrium oxide produced. [Jianshe Han, Qingyu Yang and Xiang Ye, The capriccio of rare earth extraction and separation, National Symposium on Rare Earth Chemistry and Metallurgy, 2014]. Chinese Invention Patent No. 99118261.8 disclosed a liquid-liquid extraction method for separating high-purity yttrium which used a mixture of sec-octylphenoxy substituted acetic acid (CA12) and a monobasic phosphoric (phosphonic) acid or its monothio derivatives (such as P204, P507, Cyanex 272, Cyanex302, etc.) as extractant, which contributed to solve the emulsification problem of naphthenic acid system. However, the above-described method still has a problem of concentration decrease of organic phase. Chinese Invention Patent No. CN201210290516 disclosed a non-saponification process for extracting and separating rare earths, which used a composite solvent as a composite extractant obtained by mixing an acidic phosphonic (phosphorus) extractant such as P507 or P204 with an amine extractant such as N235. It directly extracted and separated rare earths without saponification, but still required a back-extraction with inorganic acids. In all the above-described extraction processes acids or alkalis are used, so that the extraction is carried out under high acidic (low pH) conditions, thus lowering the extraction efficiency and causing environmental contamination with acids or alkalis.

Contents of the Invention

An object of the present invention is to overcome the above disadvantages of the prior art by providing an extractant for the extraction and separation of yttrium. Said extractant has a high separation factor, good extraction phenomena, and stable organic phase, and did not show a significant concentration decrease after a long-term recycling use.

Another object of the present invention is to provide a method for the extraction and separation of yttrium. The method comprises the extraction under low acidic conditions without the saponification of organic phase, and the washing and back-extraction can be realized with water, thus achieving a significant saving in acid and alkali consumption. It can also achieve a high separation factor for rare earths and good extraction phenomena.

In view of the above, the invention provides the following technical solutions:

An extractant for the extraction and separation of yttrium, wherein said extractant is one or a mixture of ionic liquid-based compounds represented by the following formula (1):

Formula (1)

wherein,

X is P or N;

$R_1$, $R_2$, $R_3$ and $R_4$ may be the same or different, and are each independently selected from the group consisting of substituted or unsubstituted branched or linear alkyl, substituted or unsubstituted aryl; said substituent is a branched or linear alkyl, a branched or linear alkoxy, or halogen.

According to the present invention, the branched or linear alkyl group of $R_1$, $R_2$, $R_3$ and $R_4$ is preferably selected from the group consisting of $C_1$-$C_{20}$ branched or linear alkyl, more preferably methyl, ethyl, n-butyl, n-hexyl, n-decyl, or tetradecyl; said aryl group is preferably a phenyl group.

According to the present invention, two or three or four groups of $R_1$, $R_2$, $R_3$ and $R_4$ are the same. For example, three of $R_1$, $R_2$, $R_3$ and $R_4$ are n-hexyl groups, and the other is an n-tetradecyl group; or all of $R_1$, $R_2$, $R_3$ and $R_4$ are n-butyl groups.

The invention also provides the further following technical solutions:

A method for the extraction and separation of yttrium, comprising the following steps:

(1) mixing the above extractant with a diluent to obtain an organic phase;

(2) mixing the organic phase obtained in step (1) with a rare earths solution containing yttrium to undergo selective extraction, so that yttrium is remained in the aqueous phase while the other rare earths move into the organic phase.

Preferably, said method further comprises the following step:

(3) back-extracting the organic phase obtained in step (2) using an inorganic acid, so that the rare earths in the organic phase move into the aqueous phase.

Preferably, the organic phase after back-extraction in said step (3) can be used repeatedly in the step (2) to replace the organic phase obtained in step (1). Preferably, the times of the repeated use is at least 15 times.

Preferably, the volume ratio of extractant to diluent in said step (1) is 1-50:99-50, more preferably 10-40:90-60.

Preferably, said diluent is one or more selected from alkanes or aromatic hydrocarbons. Preferably, said alkane is one or more selected from heptane, octane, cetane, aviation kerosene or 260# solvent kerosene, and said aromatic hydrocarbon is one or more selected from benzene, toluene or xylene.

Preferably, said inorganic acid is one selected from hydrochloric acid, nitric acid or sulfuric acid, more preferably hydrochloric acid or nitric acid, and most preferably hydrochloric acid.

According to the invention, the molar concentration of said inorganic acid ranges between 0.005 and 1.0 mol/l, preferably between 0.01 and 0.5 mol/l.

The invention further provides the following technical solutions:

A method for the extraction and separation of yttrium, comprising the following steps: (S1) mixing an extractant and a diluent to obtain an organic phase; (S2) mixing the organic phase obtained in step (S1) with a rare earth feed liquid containing yttrium to undergo a selective extraction, so that yttrium is remained in the aqueous phase while the yttrium-poor rare earths move into the organic phase; (S3) washing the organic phase obtained in step (S2) with deionized water; and (S4) back-extracting the organic phase obtained in step (S3), so that the yttrium-poor rare earths in the organic phase move into the aqueous phase.

Wherein, the extractant is one or a mixture of ionic liquid-based compounds represented by $A^+B^-$, wherein $A^+$ is represented by the following formula (2),

Formula (2)

in the formula (2), X is P or N; $R_1$, $R_2$, $R_3$ and $R_4$ may be the same or different, and are each independently selected from the group consisting of substituted or unsubstituted branched or linear alkyl, substituted or unsubstituted aryl; said substituent is a branched or linear alkyl, a branched or linear alkoxy or halogen;

Said $B^-$ has a structure represented by the following formula (3), or it is a mixture of compounds represented by the formula (4) (also being referred to as naphthenic acid in the art, denoted by NA), Formula (3)

Formula (4)

In the formula (4), $R_5$ is $CH_3$ or H, p=6-8.

Furthermore, the organic phase after back-extraction in step (S4) may be repeatedly used in step (S2) to replace the organic phase obtained in step (S1); preferably, the times of the repeated use is at least 15 times.

Furthermore, the volume ratio of extractant to diluent in said step (S1) is 1-50:99-50, more preferably 10-45:90-60.

Furthermore, in the formula (2), the branched or linear alkyl group of $R_1$, $R_2$, $R_3$ and $R_4$ is preferably selected from the group consisting of $C_1$-$C_{20}$ branched or linear alkyl, more preferably methyl, ethyl, n-butyl, n-hexyl, n-octyl, n-decyl or tetradecyl; the aryl group of $R_1$, $R_2$, $R_3$ and $R_4$ is preferably phenyl group.

Furthermore, in the formula (2), two or three or four groups of $R_1$, $R_2$, $R_3$ and $R_4$ can be the same. For example, three of $R_1$, $R_2$, $R_3$ and $R_4$ are n-hexyl groups, and the other is an n-tetradecyl group; or three of $R_1$, $R_2$, $R_3$ and $R_4$ are n-octyl groups, and the other is a methyl group; or all of $R_1$, $R_2$, $R_3$ and $R_4$ are n-butyl groups.

Furthermore, the extractant is one or more selected from methyl tri-n-octyl quaternary ammonium sec-octylphenoxy substituted acetic acid, tri-n-hexyl-n-tetradecyl quaternary phosphonium sec-octylphenoxy substituted acetic acid, methyl tri-n-octyl quaternary ammonium naphthenic acid and tri-n-hexyl n-tetradecyl quaternary phosphonium naphthenic acid.

Furthermore, the diluent is one or more selected from alkanes or aromatic hydrocarbons. Preferably, said alkane is one or more selected from heptane, octane, cetane, aviation kerosene or 260# solvent kerosene, and said aromatic hydrocarbon is one or more selected from benzene, toluene and xylene.

Moreover, the flow ratio of the organic phase, the rare earth feed liquid containing yttrium, the water for washing and the water for back-extraction is 1-6:1:0.5-3:0.5-12.

Preferably, the entire extraction process of the above method is carried out in a mixer-settler. It comprises n extraction stages, m wash stages and k back-extraction stages, wherein n=5-25, m=5-25 and k=2-8. Preferably, the organic phase is added at the first stage, the rare earth feed liquid containing yttrium is added at the $n^{th}$ stage, the water for washing is added at the $(n+m)^{th}$ stage, and the water for back-extraction is added at the $(n+m+k)^{th}$ stage. In a particular embodiment according to the invention, n=13, m=8 and k=5, wherein the flow ratio of the organic phase, the rare earth feed liquid containing yttrium, the water for washing and the water for back-extraction is 3:1:1.5:3. The mixing time of extraction is 4 minutes. The product of yttrium elutes from the first stage outlet, and after back-extraction, the organic phase directly returns to the first stage without saponification.

In another embodiment according to the invention, n=15, m=10 and k=5, wherein the flow ratio of the organic phase, the rare earth feed liquid containing yttrium, the water for washing and the water for back-extraction is 6:1.8:2.5:8. The mixing time of extraction is 5 minutes. The product of yttrium elutes from the first stage outlet, and after back-extraction the organic phase directly returns to the first stage without saponification.

In comparison with prior art, the invention provides an extractant and a method for the extraction and separation of yttrium, which have the following advantages: ① the extractant has a simple composition, the formulated organic phase has stable properties, and the extractant has a loss ratio lower than 0.5%; ② the extractant has a good separation effect on yttrium; ③ because of the particular phase transition effect of the ionic liquid, the back-extractant is more prone to move into the organic phase, so that the back-extraction efficiency can be significantly increased and the concentration of the used back-extractant can be much lower than 2.0 mol/l of the prior art. The optimal concentration is 0.2 mol/l which can achieve approximately 100% of the back-extraction efficiency; ④ the present invention uses ionic liquid saponification so that the production of wastewater can be avoided during the extraction process. Therefore, the invention provides an extractant with simple composition and stable performance, and a high efficient method for the extraction and separation of yttrium.

In comparison with prior art, the invention further provides a method for the extraction and separation of yttrium, which have the following advantages: ① The extraction can be carried out under low acidic (high PH) conditions, and after extraction, the purity of yttrium in the aqueous phase can be up to 99.9%, showing a very good yttrium selectivity of the extraction and separation. ② According to the present process, both the washing and back-extraction steps use deionized water, rather than inorganic acid or alkali. ③ The organic phase can be recycled without saponification, and after 15 extraction cycles, no significant change of the concentration of the organic phase has been observed. ④ No ammonia-nitrogen wastewater was produced in the process of extraction. c for the extraction and separation of yttrium.

SPECIFIC MODE FOR CARRYING OUT THE INVENTION

[Extractant and Method for Extraction and Separation]

As described above, the invention provides an extractant and a method for the extraction and separation of yttrium, comprising the following steps of: (1) mixing the above-mentioned extractant and a diluent to obtain an organic phase; (2) mixing the organic phase obtained in step (1) with a rare earth feed liquid containing yttrium to undergo a selective extraction, so that yttrium is remained in the aqueous phase while the yttrium-poor rare earths move into the organic phase. Preferably, said method further comprises: (3) back-extracting the organic phase obtained in step (2) using an inorganic acid, so that the rare earths in the organic phase move into the aqueous phase.

In the present invention, the cation of ionic liquid-based compound is selected from quaternary ammonium or quaternary phosphonium, and the anion is the sec-octylphenoxy substituted acetate. There is no limitation on the sources of the precursors of said cations and anion. For example, said anion may be derived from sec-octylphenoxy acetate. Preferably, the extractant (i.e. said ionic liquid-based compound) for the extraction and separation of yttrium is synthesized by acid-base neutralization process.

In the present invention, there is no limitation on the mixing manners of said extractant and said diluent to obtain the organic phase. All mixing manners well known to those skilled in the art can be used.

The rare earth feed liquid containing yttrium used in the present invention can be a nitric acid solution of rare earths containing yttrium, or a hydrochloric acid solution of rare earths containing yttrium, which the present invention is not limited to.

The temperature for the extraction according to the present invention is preferably 20° C.-35° C., more preferably 23° C.-30° C.; said extraction time is preferably 5-10 min. The temperature for the back-extraction is preferably 20° C.-35° C., more preferably 23° C.-30° C.; said back-extraction time is preferably 5-10 min.

After the extraction and separation process are completed, the mixed rare earth elements in the raffinate or the back-extraction solution of the present invention are preferably determined by ICP-MS method, with specific reference to GB/T 18114.8-2010 chemical analysis methods of rare earth concentrates-part 8: determination of fifteen rare earth oxide relative contents.

Single rare earth elements are determined by Arsenazo (III) colorimetry.

The calculation formulae of extraction efficiency (E), distribution ratio (D), back-extraction efficiency (S) and separation factor (β) are described as follows:

$$E\% = \frac{[M]_t - [M]_a}{[M]_t}$$

$$D = \frac{[M]_t - [M]_a}{[M]_a}$$

$$S\% = \frac{[M]_{aq,a}}{[M]_{org,t}} \times 100\%$$

$$\beta = \frac{D_1}{D_2}$$

wherein $[M]_t$ and $[M]_a$ respectively represent the initial concentration of rare earth ions and the equilibrium concentration of rare earth ions in aqueous phase; $[M]_{aq,a}$ and $[M]_{org,t}$ respectively represent the concentration of rare earths in the back-extraction solution and the concentration of rare earths in the organic phase; $D_1$ and $D_2$ are the distribution ratio of the extractant on two different rare earths.

[Another Extraction and Separation Method]

As described above, the invention provides a method for the extraction and separation of yttrium, comprising the following steps: (S1) mixing an extractant and a diluent to obtain an organic phase; (S2) mixing the organic phase obtained in step (S1) with a rare earth feed liquid containing yttrium to undergo a selective extraction, so that yttrium is remained in the aqueous phase while the yttrium-poor rare earths move into the organic phase; (S3) washing the organic phase obtained in step (S2) with deionized water; and (S4) back-extracting the organic phase obtained in step (S3), so that the yttrium-poor rare earths in the organic phase move into the aqueous phase. In step (S3) of the extraction and separation method, deionized water is used to wash the organic phase to improve separation factors of yttrium with other rare earths, which is contributed to increase purity and yield of yttrium product.

As can be seen from the above, according to the extraction and separation process provided herein, only deionized water, rather than inorganic acid and alkali, is used in the washing step (S3) and the back extraction step (S4), so that the extraction can be carried out under low acidic (high PH) conditions. Thus a high extraction efficiency can be achieved without ammonia wastewater produced in the extraction process, thereby achieving zero environmental pollution.

Since the selected extractant of the present invention has stable properties, the organic phase prepared from the extractant can achieve decreased loss during recycling processes and return to the initial state completely. Therefore, the organic phase after back-extraction in said step (S4) can be repeatedly used in the step (S2) to replace the organic phase obtained in the step (S1). Preferably, the times of the repeated use are at least 15 times.

In the present invention, the cation of the ionic liquid-based compound is selected from quaternary ammonium or quaternary phosphonium, and the anion is the sec-octylphenoxy acetate ion or the naphthenic acid ion. The sources of the precursors of said cation and anion are not limited, for example, said anion comes from sec-octylphenoxy acetate or naphthenate. There is no limitation on the sources of the precursors of said cations and anion in the present application. For example, the anion can be derived from sec-octylphenoxy acetate or naphthenates. The extractant of the present invention (i.e. said ionic liquid-based compound) is preferably synthesized by acid-base neutralization process.

In accordance with the present invention, the extractant is one or more selected from methyl tri-n-octyl quaternary ammonium sec-octylphenoxy substituted acetic acid (code [N263][CA12]), tri-n-hexyl-n-tetradecyl quaternary phosphonium sec-octylphenoxy substituted acetic acid (code [P66614][CA12]), methyl tri-n-octyl quaternary ammonium naphthenic acid (code [N263][NA]) and tri-n-hexyl-n-tetradecyl quaternary phosphonium naphthenic acid (code [P66614][NA]).

Because the above-mentioned extractant has advantages such as simple synthesis, high separation selectivity on rare earths, no saponification, the extraction method according to the present invention uses deionized water instead of acid or alkali in washing and back extraction steps, thereby reducing the acid consumption to the utmost extent, and thus minimizing production cost and reducing the production of "three wastes". By the extraction and separation method of the present invention, the product can be achieved in high yield and the yttrium finally separated can achieve a high purity, even a purity of up to 99.9%.

In the present invention, there is no limitation on the mixing manners of said extractant and said diluent to obtain the organic phase. All mixing manners well known to those skilled in the art can be used.

According to the present invention, the volume ratio of extractant to diluent in said step (S1) can be, for example, 1-50:99-50. Preferably it can also be 10-45:90-60. The diluent is one or more selected from alkanes or aromatic hydrocarbons. Preferably, the alkane is one or more selected from heptane, octane, cetane, aviation kerosene or 260# solvent kerosene, and the aromatic hydrocarbon is one or more selected from benzenande, toluene and xylene.

The rare earth feed liquid containing yttrium used in the present invention can be a nitric acid solution of rare earths containing yttrium, or a hydrochloric acid solution of rare earths containing yttrium, which the present invention is not limited to.

In accordance with the present invention, a flow ratio of the organic phase, the rare earth feed liquid containing yttrium, the water for washing and the water for back-extraction is 1-6:1:0.5-3:0.5-12.

The temperature for the extraction of the present invention is preferably 20° C.-55° C.; the extraction time is preferably 2-10 minutes. The back-extraction temperature is preferably 20° C.-55° C.; the back-extraction time is preferably between 2-10 minutes.

After the extraction and separation process are completed, the mixed rare earth elements in the raffinate or the back-extraction solution of the present invention are preferably determined by ICP-MS method, with specific reference to GB/T 18114.8-2010 chemical analysis methods of rare earth concentrates-part 8: determination of fifteen rare earth oxide relative contents.

Hereinafter, the present invention will be further illustrated detailedly with reference to the examples and figures. However, those skilled in the art would understand that the protection scopes of the present invention are not limited to the following examples. According to the disclosure of the present invention, those skilled in the art would recognize that all changes and modifications based on the described examples, without departing from the technical features and scope provided in the technical solutions of the present invention, should belong to the protection scope of the present invention. All the materials used in the following examples, unless otherwise specified, are commercially available products.

Example 1

Synthesis of [N4, 4, 4, 4][CA12]

In a 125 ml separatory funnel, 0.006 mol tetrabutylammonium bromide (denoted by [N4, 4, 4, 4]Br) was added into 40 ml methanol, and then strong alkaline anion exchange resin (75 ml) was added to give tetrabutylammonium hydroxide (denoted by [N4444]OH) solution. 0.006 mol sec-octylphenoxy substituted acetic acid (code CA12) was added in the solution and the obtained mixture was stirred at room temperature for 6 h until the solution was neutral. Methanol and water were removed in a rotary evaporator at 70° C., and the product was dried in a vacuum oven at 70° C. for 12 h to give a viscous liquid [N4,4,4,4][CA12] with a yield of 95%.

Example 2

Synthesis of [P6, 6, 6, 14] [CA12]

In a 250 ml separatory funnel, tetradecyl(trihexyl)phosphonium chloride (denoted by [P6,6,6,14]Br, code CYPHOS IL 101) (0.012 mol) was added into 80 ml methanol and then 150 ml strong alkaline anion exchange resin was added to give tetradecyl(trihexyl)phosphonium hydroxide (denoted by [P6,6,6,14]OH) solution. 0.012 mol Sec-octylphenoxy substituted acetic acid (code CA12) was added in the solution and the mixture was stirred at room temperature for 6 h until the solution was neutral. Methanol and water were removed in a rotary evaporator at 70° C., and the product was dried in a vacuum oven at 70° C. for 12 h to give a viscous liquid [P6,6,6,14][CA12] with a yield of 94%.

Example 3

Preparation of the organic phase: [P6, 6, 6, 14][CA12] synthesized in the Example 2 was mixed with toluene to prepare the organic phase, and the concentration of [P6, 6, 6, 14][CA12] was 0.10 mol/l.

Preparation of the feed liquid: the solutions of yttrium, holmium, erbium, thulium, ytterbium and lutetium were separately taken, and diluted hydrochloric acid was added to prepare a feed liquid containing yttrium in which the concentration of a single rare earth is 0.06 mol/l, wherein NaCl solution was 0.5 mol/l, pH is 3.2, and the total concentration was 0.36 mol/l.

The organic phase and the feed liquid were mixed in a volume ratio of 1:1 and then extracted at room temperature with the extraction stage is 1. After the extraction was completed, extraction efficiency (E), distribution ratio (D) and separation factor ($\beta$) were calculated. Extraction efficiency (E) and distribution ratio (D) were shown in Table 1, and separation factor ($\beta$) was indicated in FIG. 1. After 15 times repeated uses, the properties of organic phase were stable and the extraction phenomena were good.

TABLE 1

| [P6, 6, 6, 14] [CA12] System | Y | Ho | Er | Tm | Yb | Lu |
|---|---|---|---|---|---|---|
| E % | 18.0 | 26.5 | 28.6 | 35.2 | 43.8 | 47.6 |
| D | 0.220 | 0.360 | 0.401 | 0.542 | 0.781 | 0.908 |

Comparative Example 1

Preparation of the organic phase: Commercial sec-octylphenoxy substituted acetic acid CA12 was mixed with iso-octanol and toluene to prepare an organic phase, wherein the concentration of CA12 was 0.10 mol/l, and the volume concentration of iso-octanol was 2%.

Preparation of the feed liquid: the same as in Example 3.

The organic phase and the feed liquid were mixed in a volume ratio of 1:1, and then extracted at room temperature with the extraction stage is 1. After the extraction was completed, extraction efficiency (E), distribution ratio (D) and separation factor ($\beta$) were calculated. Extraction efficiency (E) and distribution ratio (D) were shown in Table 2, and separation factor ($\beta$) was indicated in FIG. 1. After 15 times repeated uses, the concentration of the organic phase decreased 25%.

TABLE 2

| CA12 system | Y | Ho | Er | Tm | Yb | Lu |
|---|---|---|---|---|---|---|
| E % | 5.3 | 6.1 | 7.3 | 9.1 | 9.5 | 2.0 |
| D | 0.056 | 0.065 | 0.079 | 0.100 | 0.105 | 0.021 |

Figure 1:
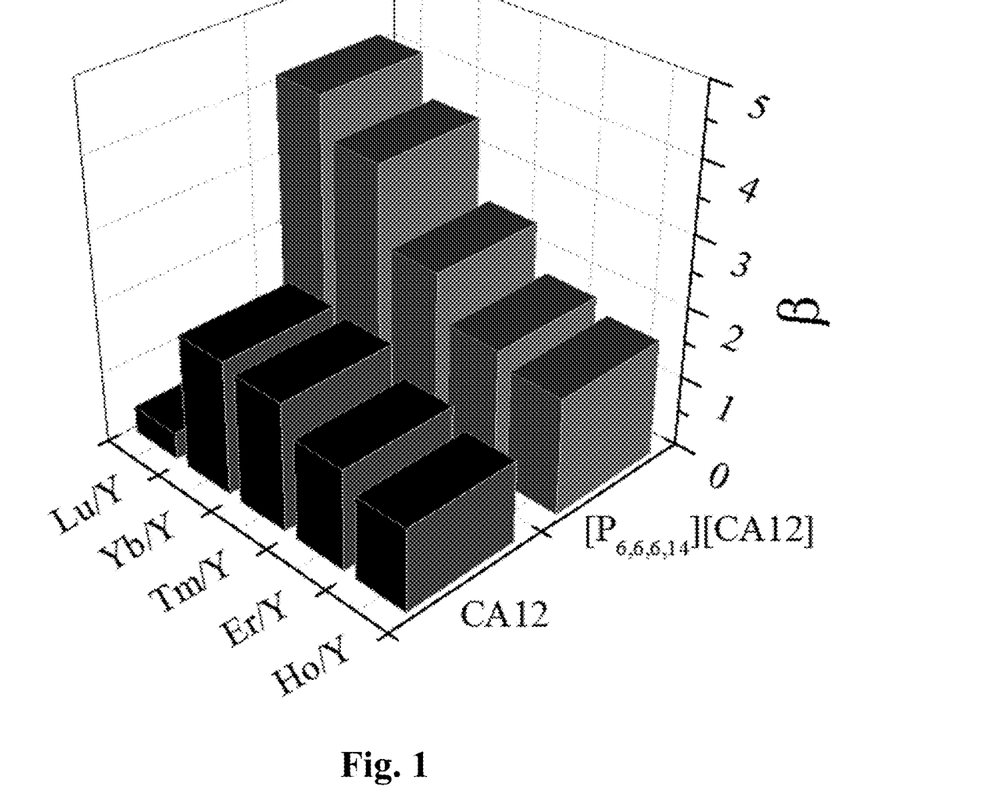
FIG. 1 shows the separation factors of the extractant [P6, 6, 6, 14] [CA12] of the invention and a prior art extractant CA12 on various rare earths.

As shown in FIG. 1, the yttrium selectivity of [P6,6,6,14][CA12] extraction system was excellent. Under the experimental conditions, the yttrium selectivity and relative stability of the organic phase were significantly superior to the CA12 extraction system.

Example 4

Preparation of the organic phase: [N4, 4, 4, 4][CA12] synthesized in Example 1 and [P6,6,6,14][CA12] synthesized in Example 2 was mixed in a mole ratio of 1:1 to prepare a mixed extractant. The mixed extractant was then mixed with toluene to prepare an organic phase, wherein the concentration of [N4,4,4,4][CA12] was 0.05 mol/l, and the concentration of [P6,6,6,14] [CA12] was 0.05 mol/l.

The other steps were the same as in Example 3.

The extraction efficiency (E), distribution ratio (D) and separation factor ($\beta$) of the above-described extraction were, respectively, similar to those in Example 3.

Examples 5-7

Preparation of the organic phase: [P6, 6, 6, 14] [CA12] synthesized in Example 2 was mixed with toluene to prepare an organic phase, and the concentration of [P6,6,6,14] [CA12] was 0.07 mol/l.

Preparation of the feed liquid: the solution of yttrium was taken and then diluted hydrochloric acid was added to prepare a feed liquid containing yttrium with a concentration of 0.002 mol/l, wherein NaCl solution was 0.5 mol/l and pH is 3.2.

The above-described organic phase of [P6, 6, 6, 14] [CA12] and the feed liquid containing yttrium were mixed with a volume ratio of 1:1 and then extracted. The concentration of yttrium loaded in the organic phase was 0.0012 mol/l. The loaded organic phase was mixed with the back-extraction solutions with various concentrations respectively in a volume ratio of 1:1, and then back-extracted at room temperature. Said back-extraction solutions were hydrochloric acid solution with different concentrations of 0.01, 0.02 and 0.2 mol/l respectively. After the back-extraction was completed, back-extraction efficiency (S) was calculated. The results showed that the back-extraction efficiencies of the solutions with different concentrations of 0.01, 0.02 and 0.2 mol/l were 92%, 94% and 99%, respectively.

Examples 8-10

The extractant was replaced with [N4, 4, 4, 4][CA12] in Example 1, and the other conditions were the same as those described in Examples 5-7. The results showed that the back-extraction efficiencies of the solutions with different concentrations of 0.01, 0.02 and 0.2 mol/l were 90%, 93% and 98%, respectively.

Examples 11-13

Preparation of the organic phase: [P6, 6, 6, 14][CA12] synthesized in Example 2 was mixed with toluene to prepare an organic phase, and the concentration of [P6,6,6,14] [CA12] was 0.03 mol/l.

Preparation of the feed liquid: the solution of yttrium was taken and diluted hydrochloric acid was then added to prepare a feed liquid containing yttrium with concentrations of 0.002 mol/l, 0.004 mol/l and 0.006 mol/l respectively, wherein NaCl solution was 0.5 mol/l and pH is 3.2. The above-described organic phase of [P6,6,6,14][CA12] and the feed liquid containing yttrium with concentrations of 0.002 mol/l, 0.004 mol/l and 0.006 mol/l were separately mixed in a volume ratio of 1:1, and then extracted. The loss ratios of the extractants were determined. The results showed that the concentrations of total phosphorus in the solution after extraction were 0.72 mg/l, 0.73 mg/l and 0.77 mg/l, less than the emission standard of phosphorus in the pollutants from rare earth industry provided in GB/T 26451-2011 (indirect phosphorus emission limit value: 5 mg/l).

Examples 14-16

The extractant was replaced with [N4, 4, 4, 4][CA12] in Example 1, and the other conditions were the same as those described in Examples 11-13. The results showed that the concentrations of total nitrogen in the solution after extraction were 0.75 mg/l, 0.75 mg/l and 0.80 mg/l respectively, less than the emission standard of nitrogen in the pollutants from rare earth industry provided in GB/T 26451-2011 (indirect phosphorus emission limit value: 70 mg/l).

Example 1'

1) Preparation of extractant [N263][CA12]

1.62 kg methyl tri-n-octyl ammonium chloride (N263, 4 mol), 1.06 kg sec-octylphenoxy substituted acetic acid (CA12, 4 mol), 0.16 kg sodium hydroxide (4 mol) and 1 kg methanol were mixed and stirred at 60° C. for 2 h. After cooling, 0.18 kg sodium chloride crystals were filtered out. To the organic phase, the equal volume of water was added and then washed with the water for three times, and dried under vacuum at 100° C. for 12 h to give 2.48 kg ionic liquid extractant [N263][CA12] with a yield of 98.1%.

2) Preparation of the organic phase: 0.54 g extractant obtained in step 1) was mixed with 1.26 kg toluene to prepare an organic phase with the concentration of [N263][CA12] was 0.40 mol/l.

3) Preparation of the rare earth feed liquid containing yttrium: the concentrated rare earth feed liquid containing yttrium was diluted with water so that pH is 2 and total concentration is 0.2 mol/l. The composition was shown in Table 3.

TABLE 3

| Composition of the rare earth feed liquid containing yttrium | | | | | | | |
|---|---|---|---|---|---|---|---|
| Rare earth oxide | La—Dy | Y | Ho | Er | Tm | Yb | Lu |
| Weight ratio (%) | 0 | 87.3 | 3.6 | 4.73 | 1.35 | 2.7 | 0.3 |

Figure 2:
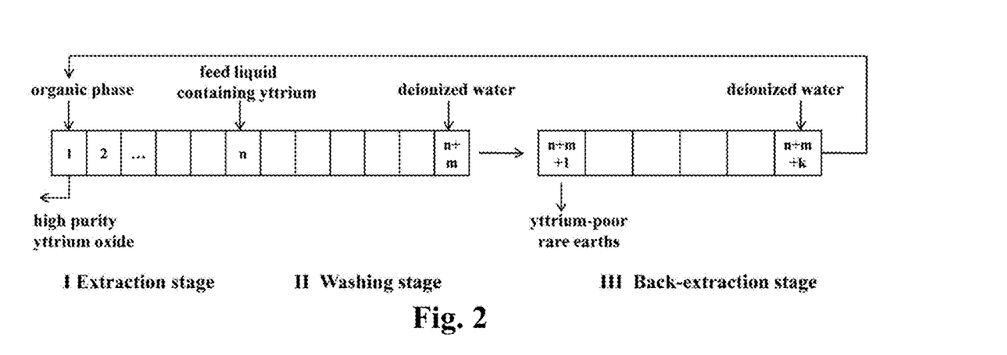
FIG. 2 is a schematic view of an exemplary embodiment of the extraction and separation process in accordance with the present invention.

4) Extraction and separation: as shown in FIG. 2, the entire extraction process was performed in a mixer settlers containing 13 extraction stages (n=13), 8 wash stages (m=8) and 5 back-extraction stages (k=5). The organic phase was added at the first stage, the rare earth feed liquid containing yttrium was added at the $13^{th}$ stage, the water for washing was added at the $21^{st}$ stage, and the water for back-extraction was added at the $26^{th}$ stage, wherein the flow ratio of the organic phase, the rare earth feed liquid containing yttrium, the water for washing and the water for back-extraction was 3:1:1.5:3. The mixing time of extraction was 4 minutes. The product of yttrium eluted from the first outlet, and after back-extraction the organic phase directly returns to the first stage without saponification. After 18 times recycling uses, the properties of the organic phase were stable and the extraction phenomena were good. After half a month of operation, the extraction system reached equilibrium. The contents of various components of the aqueous phase at the first stage after extraction and separation were specifically shown in Table 4. In the aqueous phase at the first stage, yttrium purity of 99.8% was achieved with respect to other rare earths.

TABLE 4

| Contents of various components of the aqueous phase at the first stage | | | | | | | |
|---|---|---|---|---|---|---|---|
| Rare earth oxide | La—Dy | Y | Ho | Er | Tm | Yb | Lu |
| Weight ratio (%) | 0 | 99.8 | 0.07 | 0.09 | <0.01 | <0.01 | <0.01 |

Comparative Example 1'

Preparation of the organic phase: Commercial sec-octylphenoxy substituted acetic acid was mixed with iso-octanol and toluene to prepare an organic phase, wherein the concentration of CA12 was 0.40 mol/l, and the volume concentration of iso-octanol was 10%.

Preparation of the feed liquid: the same as in Example 1'.

The organic phase, the rare earth feed liquid containing yttrium, the water for washing and the water for back-extraction were mixed according to a flow ratio of 3:1:1.5:3, and extracted at room temperature. The extraction and separation steps were the same as Example 1'. The contents of various components of the aqueous phase at the first stage after extraction and separation were shown in Table 5. In the aqueous phase at the first stage, yttrium purity was only 93.7% with respect to other rare earths. The concentration of the organic phase decreased 15% after being recycling used one time.

TABLE 5

| Contents of various components of the aqueous phase at the first stage | | | | | | | |
|---|---|---|---|---|---|---|---|
| Rare earth oxide | La—Dy | Y | Ho | Er | Tm | Yb | Lu |
| Weight ratio (%) | 0 | 93.7 | 1.9 | 2.3 | 0.67 | 1.27 | 1.14 |

The comparison result showed that the yttrium selectivity of the [N263][CA12] system was excellent. Under the experimental conditions, the yttrium selectivity and the stability of the organic phase of the [N263][CA12] system were significantly superior to those of the CA12 system.

Example 2'

1) Preparation of extractant [P66614][NA]: 2.08 kg Trihexyl tetradecyl quaternary phosphonium chloride (P66614, 4 mol), 1.29 kg naphthenic acid (NA, 4 mol), 0.16 kg sodium hydroxide (4 mol) and 1 kg methanol were mixed and stirred at 60° C. for 2 h. After cooling, 0.17 kg sodium chloride crystals was filtered out. To the organic phase, the equal volume of water was added and then washed with the water for three times, and dried under vacuum at 100° C. for 12 h to give 2.25 kg ionic liquid extractant [P66614][NA] with a yield of 96.3%.

2) Preparation of the organic phase: 0.81 g ionic liquid extractant [P66614][NA] obtained in step 1) was mixed with 1.09 kg 260# solvent kerosene to prepare an organic phase with a concentration of 0.50 mol/l.

3) Preparation of the rare earth feed liquid containing yttrium: the concentrated rare earth solution containing yttrium was diluted with water to a pH of 6.0 and a total concentration of 0.4 mol/l. The composition was shown in the following Table 6.

TABLE 6

Composition of the rare earth feed liquid containing yttrium

| Rare earth oxide | Y | La—Dy | Ho | Er | Tm | Yb | Lu |
|---|---|---|---|---|---|---|---|
| Weight ratio (%) | 36.8 | 10.5 | 15.8 | 19.5 | 5.6 | 10.6 | 1.2 |

4) Extraction and separation: the entire extraction process was performed in a mixer settlers containing 15 extraction stages (n=15), 10 wash stages (m=10) and 5 back-extraction stages (k=5). The organic phase was added at the first stage, the rare earth feed liquid containing yttrium was added at the 15$^{th}$ stage, the water for washing was added at the 25$^{st}$ stage, and the water for back-extraction was added at the 30$^{th}$ stage. The flow ratio of the organic phase, the rare earth feed liquid containing yttrium, the water for washing and the water for back-extraction was 3.3:1:1.4:4.5. The mixing time of extraction was 5 minutes. After one month of operation, the extraction system reached equilibrium. The contents of various components of the aqueous phase at the first stage after extraction and separation were specifically shown in Table 7. The product of yttrium eluted from the first outlet, and the yttrium purity of 99.9% was achieved with respect to other rare earths. After back-extraction, the organic phase can directly return to the first stage without saponification. After 16 times recycling uses, no significant decrease was observed. Thus it was clear that the organic phase can be recycling used, has stable properties and lead to good extraction phenomena.

TABLE 7

Contents of various components of the aqueous phase at the first stage

| Rare earth oxide | Y | La—Dy | Ho | Er | Tm | Yb | Lu |
|---|---|---|---|---|---|---|---|
| Weight ratio (%) | 99.9 | <0.001 | 0.05 | 0.05 | <0.001 | <0.001 | <0.001 |

The invention claimed is:

1. A method for the extraction and separation of yttrium, comprising:
   (1) mixing an extractant with a diluent to obtain an organic solution,
   wherein the extractant is a compound or a mixture of compounds of formula (1):

Formula (1)

wherein,
   X is P or N; and
   all of $R_1$, $R_2$, $R_3$, and $R_4$ are n-butyl, or one of $R_1$, $R_2$, $R_3$, and $R_4$ is n-tetradecyl and the other three of $R_1$, $R_2$, $R_3$, and $R_4$ are n-butyl;
   (2) in a first extraction step, mixing the organic solution obtained in step (1) with an aqueous solution containing yttrium and other rare earth compounds to undergo selective extraction, so that yttrium remains in an aqueous phase while the other rare compounds are extracted into an organic phase; and
   (3) in a back-extraction step, mixing the organic phase obtained from step (2) with an aqueous inorganic acid solution to extract the other rare earth compounds from the organic phase into the aqueous inorganic acid solution, wherein a molar concentration of the inorganic acid in the aqueous inorganic acid solution is 0.005 mol/l to 0.5 mol/l.

2. The method for the extraction and separation of yttrium of claim 1, further comprising a further extraction step, wherein the rare earth-poor organic phase obtained from the back-extraction step is mixed with a second aqueous solution containing yttrium and other rare earth compounds to extract the other rare earth compounds into the rare earth-poor phase obtained from the back-extraction step.

3. A method of the extraction and separation of yttrium from an aqueous rare earth feed liquid, comprising the following steps:
   (S1) mixing an extractant and a diluent to obtain an organic solution;
   (S2) mixing the organic solution obtained in step (S1) with the aqueous rare earth feed liquid containing yttrium to undergo a selective extraction, so that yttrium remains in an aqueous phase while the yttrium-poor rare earths are extracted into an organic phase;
   (S3) washing the organic phase obtained in step (S2) with deionized water; and
   (S4) back-extracting the organic phase obtained in step (S3) with water so that the yttrium-poor rare earths in the organic phase is extracted into water,
   wherein an extractant is one compound or a mixture of ionic liquid-based compounds of $A^+B^-$,
   wherein $A^+$ is of formula (2) and $B^-$ is a mixture of naphthenic acids (NA) of formula (4), Formula (2)

Formula (4)

in the formula (4), $R_5$ is $CH_3$ or H, and p=6-8;
   or $A^+B^-$ is a compound or a mixture of compounds of formula (1):

Formula (1)

wherein X is P or N, all of $R_1$, $R_2$, $R_3$, and $R_4$ are n-butyl, or one of $R_1$, $R_2$, $R_3$, and $R_4$ is n-tetradecyl and the other three of $R_1$, $R_2$, $R_3$, and $R_4$ are n-butyl.

4. The method for the extraction and separation of yttrium of claim 3, wherein said diluent is selected from the group consisting of alkanes, aromatic hydrocarbons, and mixtures thereof.

5. The method for the extraction and separation of yttrium of claim 3, wherein ratios of flow rates of the organic phase, the rare earth feed liquid containing yttrium, the water for washing, and the water for back-extraction are 1-6:1:0.5-3:0.5-12, wherein the flow rate of the rare earth feed liquid containing yttrium is one.

6. The method for the extraction and separation of yttrium of claim 1, wherein the molar concentration of said inorganic acid ranges between 0.01 and 0.5 mol/l.

7. The method for the extraction and separation of yttrium of claim 1, wherein a volume ratio of the extractant to the diluent in said step (1) is 1:99 to 1.

8. The method for the extraction and separation of yttrium of claim 7, wherein the volume ratio of the extractant to the diluent in said step (1) is 1:9 to 4:6.

9. The method for the extraction and separation of yttrium of claim 1, wherein said diluent is selected from the group consisting of alkanes, aromatic hydrocarbons, and mixtures thereof.

10. The method for the extraction and separation of yttrium of claim 1, wherein said aqueous inorganic acid is hydrochloric acid, nitric acid, or sulfuric acid.

11. The method for the extraction and separation of yttrium of claim 3, a volume ratio of the extractant to the diluent in said step (S1) is 1:99 to 50:50.

12. The method for the extraction and separation of yttrium of claim 3, wherein, in the formula (2), the branched or linear alkyl group of $R_1$, $R_2$, $R_3$ and $R_4$ is selected from the group consisting of $C_1$-$C_{20}$ branched or linear alkyl, methyl, ethyl, n-butyl, n-hexyl, n-octyl, n-decyl, and tetradecyl; and wherein the aryl group of $R_1$, $R_2$, $R_3$ and $R_4$ is a phenyl group.

13. The method for the extraction and separation of yttrium of claim 3, wherein, in the formula (2), three amongst $R_1$, $R_2$, $R_3$ and $R_4$ are n-hexyl groups, and the other is an n-tetradecyl group; or three amongst $R_1$, $R_2$, $R_3$ and $R_4$ are n-octyl groups, and the other is a methyl group; or all of $R_1$, $R_2$, $R_3$ and $R_4$ are n-butyl groups.

14. The method for the extraction and separation of yttrium of claim 3, wherein the extractant is selected from the group consisting of methyl tri-n-octyl quaternary ammonium sec-octylphenoxy substituted acetic acid, tri-n-hexyl-n-tetradecyl quaternary phosphonium sec-octylphenoxy substituted acetic acid, methyl tri-n-octyl quaternary ammonium naphthenic acid, tri-n-hexyl n-tetradecyl quaternary phosphonium naphthenic acid, and mixtures thereof.

* * * * *